(12) United States Patent
Schultz et al.

(10) Patent No.: US 6,410,045 B1
(45) Date of Patent: Jun. 25, 2002

(54) DRUG DELIVERY SYSTEM FOR ANTIGLAUCOMATOUS MEDICATION

(76) Inventors: Clyde Lewis Schultz, 141 Tremont St., Boston, MA (US) 02111; Janet M. Mint, 209 Seamist Ct., Ponte Vedra, FL (US) 32082

( * ) Notice: Subject to any disclaimer, the term of this patent is extended or adjusted under 35 U.S.C. 154(b) by 0 days.

(21) Appl. No.: 09/507,437

(22) Filed: Feb. 19, 2000

Related U.S. Application Data
(60) Provisional application No. 60/121,019, filed on Feb. 22, 1999.

(51) Int. Cl.$^7$ ................................................. A61K 9/00
(52) U.S. Cl. ..................... 424/429; 424/486; 424/487; 524/86; 524/87; 524/96; 524/97
(58) Field of Search .............................. 524/86, 87, 96, 524/97; 424/429, 486, 487

(56) References Cited

U.S. PATENT DOCUMENTS

| | | | |
|---|---|---|---|
| 4,003,991 A | | 1/1977 | Krohn et al. ................... 424/81 |
| 4,070,483 A | | 1/1978 | Lerman ........................ 424/319 |
| 4,094,983 A | | 6/1978 | Bodor .......................... 424/266 |
| 4,264,493 A | * | 4/1981 | Battista ........................ 260/117 |
| 4,459,309 A | | 7/1984 | Chiou .......................... 424/300 |
| 4,484,922 A | | 11/1984 | Rosenwald .................. 604/893 |
| 4,617,299 A | | 10/1986 | Knepper ...................... 514/178 |
| 4,668,506 A | | 5/1987 | Bawa ........................... 424/429 |
| 4,713,244 A | | 12/1987 | Bawa et al. .................. 424/429 |
| 5,171,318 A | | 12/1992 | Gibson et al. ................... 623/5 |
| 5,212,168 A | | 5/1993 | Schwartz ..................... 514/179 |
| 5,401,508 A | | 3/1995 | Manesis ....................... 424/427 |
| 5,401,509 A | | 3/1995 | Robertson et al. ........... 424/427 |
| 5,401,510 A | | 3/1995 | Robertson et al. ........... 424/427 |
| 5,433,745 A | | 7/1995 | Graham et al. .................. 623/5 |
| 5,565,519 A | | 10/1996 | Rhee et al. ................... 525/54.1 |
| 5,587,175 A | * | 12/1996 | Viegas et al. ................. 424/427 |
| 5,723,131 A | | 3/1998 | Schultz et al. ............... 424/400 |
| 5,770,229 A | | 6/1998 | Tanihara et al. ............. 424/488 |
| 6,174,524 B1 | * | 1/2001 | Bawa et al. ............... 424/78.04 |
| 6,242,442 B1 | * | 6/2001 | Dean et al. ................. 514/222.8 |

OTHER PUBLICATIONS

Hillman,J.S.,"Management of acute glaucoma with Pilocarpine–soaked hydrophilic lens" Brit.J.Ophthal.58 (1974) p. 674–679.

Ramer,R. and Gasset,A., "Ocular Penetration of Pilocarpine:" Ann.Ophthalmol.6, (1974) p. 1325–1327.

Montague,R. and Wakins,R., "Pilocarpine dispensation for the soft hydrophilic contact lens" Brit.J.Ophthal. 59, (1975) p. 455–458.

Hillman,J.,Masters,J. and Broad,A."Pilocarpine deliv. by hydrophilic lens in the mgmt.of acute glaucoma" Trans. Ophthal.Soc.U.K. (1975) p. 79–84.

Marmion,V.J. and Jain,M.R. "Role of soft contact lenses and delivery of drugs" Trans.Ophthal.Soc.U.K. 96 (1976) p. 319–321.

Giambattista,B.,Virno,M., Pecori–Giraldi,Pellegrino,N. and Motolese,E. "Possibility of Isoproterenol Therapy with Soft Contact Lenses: Ocular Hypotension Without Systemic Effects" Ann.Ophthalmol 8 (1976) p. 819–829.

Marmion,V.J. and Yardakul,S. "Pilocarpine administration by contact lens" Trans.Ophthal.Soc.U.K.97, (1977) p. 162–3.

Arthur,B.W.,Hay,G.J.,Wasan,S.M. and Willis,W.E. "Ultrastructural Effects of Topical Timolol on Rabbit Cornea" Arch.Ophthalmol.vol. 10 (1983) p. 1607–1610.

Wilson,M.C. and Shields,M.B. "A Comparison of Clinical Variations of theIridocorneal Endothelial Syndrome" Arch.Ophthalmol. vol. 107, (1989) p. 1465–1468.

Fristrom,B. "A 6–month, randomized, double–masked comparison of latanoprost with timolol in patients with open angle glaucoma or ocular hypertension" Acta Opthalmol. Scand. 74:140–144 (1996).

Bawa,R., "Ocular Inserts", Opthalmic Drug Delivery Systems, vol. 58, (1993), Marcel Dekker, Inc. NY,NY. p. 223–257.

* cited by examiner

*Primary Examiner*—Peter D. Mulcahy
(74) *Attorney, Agent, or Firm*—Clark & Elbing LLP

(57) ABSTRACT

A drug delivery system for antiglaucomatous medications utilizing a polymeric hydrogel which can absorb an ophthalmic medication which can then be transferred into the ocular fluid of the eye.

18 Claims, No Drawings

DRUG DELIVERY SYSTEM FOR ANTIGLAUCOMATOUS MEDICATION

RELATED U.S. APPLICATION DATA

This present application claims priority to U.S. Provisional Patent Application Ser. No. 60/121,019 filed on Feb. 22, 1999. The entire teachings of this application are incorporated herein by reference.

REFERENCES CITED

U.S. PATENT DOCUMENTS

| | | | |
|---|---|---|---|
| 4,617,299 | 10/1986 | Knepper | 514/178 |
| 4,668,506 | 5/1987 | Bawa | 424/429 |
| 4,713,244 | 12/1987 | Bawa | 424/429 |
| 5,212,168 | 5/1993 | Schwartz | 514/174 |
| 5,723,131 | 3/1998 | Schultz et al. | 424/400 |

STATEMENT REGARDING FEDERALLY SPONSORED RESEARCH OR DEVELOPMENT

Not Applicable.

MICROFICHE APPENDIX

Not Applicable.

FIELD OF THE INVENTION

This invention relates to a polymeric hydrogel drug delivery system for absorbed antiglaucomatous medications which can be delivered into the ocular fluid.

BACKGROUND OF THE INVENTION

Glaucoma is a progressive optic neuropathy characterized by a specific pattern of damage to the head of the optic nerve and visual field. The visual system in glaucoma is damaged by the death of nerve cells which carry the visual impulse from the eye to the brain. Once a sufficient number of nerve cells are destroyed, blind spots develop, usually beginning in the peripheral field of vision. Eventually central vision is affected. Since no treatment exists to restore these damaged nerve cells, this visual loss is irreversible. glaucoma cannot currently be cured, but can be effectively managed by medical or surgical treatment.

The single most important risk factor known for the development and or progression of glaucomatous damage is elevated intraocular pressure (IOP). Average IOP ranges between 14–22 millimeters of mercury (mmHg). A pressure of of 22 or greater is considered to be elevated. Persons with IOP of 22 or greater are carefully monitored and receive treatment to lower their IOP. In some individuals with elevated IOP no ocular damage can be detected, nonetheless, they receive treatment to restore IOP to the normal range.

Numerous ocular drug delivery systems have been developed to manage IOP, but the complex anatomy of the eye have limited their effectiveness. Medications introduced into the eye are quickly washed out of the pre corneal area by the rapid production of lacrimal fluid. Additionally, medication in the eye is poorly absorbed because of the low permeability of corneal tissue.

Currently, dosing with ophthalmic medications in the form of drops results in a pattern of brief overdose of the eye medication when the drop is initially instilled, followed by a relatively short period of therapeutic dosing, followed by an interval in which the medication level drops to a less than therapeutic value. It has been determined that the ocular side effects and the more serious systemic side effects of ophthalmic drugs are primarily related to this period of initial drug overdose.

Systemic side effects experienced by the users of beta-adrenergic blocking drugs such as timolol maleate have included cardiac arrhythmias, life threatening bronchospasm and stroke. Therefore the use of beta-adrenergic blocking agents to treat glaucoma in patients diagnosed with significant cardiac or pulmonary disease requires careful monitoring and is often precluded altogether.

Additionally, a problem in the field of glaucoma treatment is the development of resistance to the commonly used anti-glaucoma medications by patients who eventually require increasing doses of their current medications or the addition of new medications to control IOP.

Ointments, gels and high viscosity eye drops have been used to provide a longer acting formulation for anti-glaucoma medication. But these delivery systems have caused significant blurring of vision and ocular discomfort in many of those patient who have tried them. Ocular inserts have also produced substantial discomfort and often fall out of the eye of their users, after which they cannot be used again.

Another concern in the area of glaucoma treatment is the issue of patient compliance with prescribed treatment programs. Often topical delivery systems involve complicated, repetitious dosing schedules and the use of gels or drops which can be awkward and difficult to apply.

The use of conventional hydrogel contact lenses containing various medications is known in the art. However, it is not known to treat elevated intraocular pressure with dilute concentrations of timolol maleate or brimonidine tartrate which have been passively transferred in an aqueous solution to hydrogel contact lenses which were prepared by washing in saline and then briefly drying the lenses.

It is known to simply presoak soft contact lenses such as Soflens ® manufactured by Bausch & Lomb, in pilocarpine hydrochloride. However, some studies have found that this lens medicament delivery system may be unsuitable for use because the lens releases 100% of pilocarpine hydrochloride in buffered saline and distilled water in merely 1.5 and 2.5 hours respectively as disclosed in U.S. Pat. No. 4,731,244. Furthermore, while it is known in the art to simply presoak contact lenses in drug solutions, these medications commonly contain preservatives such as benzalkonium chloride, which have a greater affinity for the hydrophilic contact lens material than do the aqueous drug solutions, with the result being the production of lenses with concentrated levels of preservative which can be toxic to the corneal epithelium. (Bawa, R. Chapter 11, Ocular Inserts p.231 citing Hillman, J. S. Br.J.Opthal., 58(7):674 (1975)

In view of the many disadvantages of these prior medication delivery systems, there is still a need for a new ophthalmic medication delivery system.

It is the object of this invention to provide an ophthalmic medical agent delivery system by utilizing a polymeric hydrogel to which a dilute anti-glaucoma medication has been passively transferred and from which this medication will be gradually delivered, providing the ocular environment an extended period of contact with this absorbed medication.

BRIEF SUMMARY OF THE INVENTION

This invention relates to a polymeric composition comprising a polymeric hydrogel material containing an anti-glaucoma medication, either a solution of timolol maleate in a concentration of less than 0.25% by weight or brimonidine tartrate in a concentration of less than 0.2% by weight as an additive absorbed in the polymeric composition and transferable therefrom. The polymeric hydrogel composition containing the passively transferred anti-glaucoma medication is most useful as a contact lens. The lenses which function most effectively in this instance are those that are hydrogels containing about 38–60% water by weight. All percentages described in the present invention are by weight unless otherwise specified.

This invention further relates to a process for preparing a hydrogel contact lens for use which comprises saturating the lens in a physiologic saline solution; drying the washed lens briefly and then placing the partially desiccated lens into an aqueous solution of diluted medicament at a pH of about 7.0–7.4 for approximately 3 hours and then removing the medicated lens from solution ready for use in the ocular environment.

It is an object of this invention to provide an ophthalmic medication delivery by utilizing a polymeric hydrogel which will provide effective control of elevated IOP by utilizing diluted doses of timolol maleate or brimonidine tartrate which will be delivered to the ocular environment for a period of time longer than the current dwell time achieved by these medications when used in their presently known drop or gel formulations.

It is a further object of this invention to effectively manage elevated IOP by utilizing timolol maleate or brimonidine tartrate in dilute doses which will therefore decrease the probability that users would develop resistance to these drugs and would subsequently require increased doses or substitute medications to control IOP.

Another object of this invention is to provide an ophthalmic medication delivery system of dilute timolol maleate or brimonidine tartrate to the ocular environment which will effectively control elevated IOP, but in doses lower than those at which they are currently formulated as drops or gels to reduce the risk of systemic or ocular side effects from these drugs. This diminution in the risk of systemic side effects will enable the utilization of timolol maleate or brimonidine tartrate in some of those patients who would have been precluded from their use because of existing cardiac or pulmonary conditions.

Still another object of this invention is to provide an ophthalmic medication delivery system for dilute anti-glaucoma medications which can be administered as a single daily dose, The convenience and simplicity of this system will enhance patient compliance with antiglaucomatous therapy.

An additional object of this invention is to provide an ophthalmic medication delivery system utilizing polymeric hydrogel lenses soaked in dilute formulations of antiglaucomatous medications to produce lenses which have absorbed an effective amount of medication without being exposed to higher levels of preservatives which are presently found in the medications at their currently known doses. These lenses will therefore absorb preservatives such as benzalkonium chloride in greatly reduced amounts which will then eliminate complications arising from preservative induced corneal toxicity.

BRIEF DESCRIPTION OF THE SEVERAL VIEWS OF THE DRAWING

Not Applicable.

DETAILED DESCRIPTION OF THE INVENTION

It is known to use polymeric hydrogel compositions to as medication delivery systems. The use of polymeric hydrogels as contact lenses to dispense medications in the eye is known as disclosed in U.S. Pat. Nos. 4,617,299; 4,668,506, and 5,723,131, the teachings of which are herein incorporated by reference. It is further known to use polymeric hydrogel contact lenses to deliver antiglaucomatous medications in combination with corticosteroid medications to reduce IOP as disclosed in U.S. Pat. No. 5,212,168. Polymeric hydrogel contact lenses are also known to be used as carriers of antibiotics which are dispensed into the eye as disclosed in U.S. Pat. No. 5,723,131.

However, it is not known to use polymeric hydrogel contact lenses to which timolol maleate or brimonidine tartrate, have been passively transferred, in concentrations lower than their currently known dosages, to treat elevated IOP in humans.

Patients, previously diagnosed with elevated IOP, were used as subjects in clinical tests conducted to determine whether or not hydrogel lenses containing passively transferred dilute concentrations of timolol maleate or brimonidine tartrate could effectively control increased IOP.

A further understanding of the invention may be obtained from the following non-limiting examples.

EXAMPLE 1

A hydrogel contact lens for the right eye was prepared by washing an etafilcon A lens in a saline solution and then drying the lens briefly. This partially desiccated lens was then placed in an aqueous solution of brimonidine tartrate at a concentration 0.02% or 0.2 mg of brimonidine tartrate/ml, at a pH of 7.0–7.4 for 3 hours. This prepared lens was then tested in a patient who had previously been using one drop of a brimonidine tartrate 0.2% solution in his right eye every twelve hours and which had maintained his IOP below 20 mmHg. The IOP in this patient's left eye was normal and did not require treatment. After a 4 day washout period in which all ocular medications were discontinued, the patient's IOP rose above 22 mmHg in the right eye. The patient then wore the lens treated with the brimonidine tartrate in his right eye for 30 minutes once a day. Within 24 hours the IOP in this patient's right eye had dropped to below 20 mmHg. No signs of ocular toxicity were noted upon subsequent slit lamp examination.

EXAMPLE 2

The lenses were tested in a patient who had a history of elevated IOP in both eyes and who had been treated with one drop of 0.25% timolol maleate ophthalmic solution in both eyes every 12 hours which had controlled her IOP for approximately 2 years. Eventually her IOP rose and it was necessary to change her anti-glaucoma medication to one drop every twelve hours of 0.25% timolol maleate ophthalmic gel forming solution. Provision of this medication in a gel carrier increases the time in which the medication remains in the ocular environment which should improve the efficacy of the drug. Following this treatment approach the patient's IOP remained controlled for the next 5 years.

The patient then volunteered to test etafilcon A contact lenses which were prepared for use by washing the contact lenses in a saline solution and then drying the lenses briefly. These partially desiccated lenses were then placed in an aqueous solution of diluted timolol maleate at a concentration of 0.05% or 0.68 mg timolol maleate/ml for 3 hours. After this soaking period in which timolol maleate was passively transferred to the lenses, the lenses were subsequently worn by the patient for 30 minutes once a day. During the time this patient followed this regimen her IOP was maintained at less than 20 mmHg. Slit lamp examination after this treatment revealed no signs of ocular toxicity.

Subsequently the patient's elevated IOP was effectively managed with the administration of daily timolol maleate ophthalmic gel forming solution at one fifth of her previous dosage of this medication.

EXAMPLE 3

The medicated lenses of this invention were tested in a patient who had a history of elevated IOP and had been controlled with a daily dose of 0.5% timolol maleate ophthalmic gel forming solution in each eye for two years. However, after this two year period the patient's IOP was no longer properly controlled by this medication regimen. The patient began a four day washout period during which all anti-glaucoma medication was discontinued. The patient's IOP remained above 20 mmHg during this interval. After this period the patient then tested a set of etafilcon A hydrogel lenses which were prepared by washing them in a saline solution and then drying them briefly. These partially desiccated lenses were then soaked in a dilute, aqueous solution of timolol maleate 0.05% by concentration or 0.68 mg timolol maleate/ml for 3 hours. Timolol maleate at this concentration was passively transferred to the lenses which were then worn by the patient for 30 minutes once a day. The patient's IOP was well controlled at a level of less than 20 mmHg for at least 6 months. No signs of ocular toxicity were noted on subsequent slip lamp examination.

Subsequently the procedure of Example 3 was repeated with 4 different types of polymeric hydrogel lenses, differing particularly in polymer type or water content. Each of the 4 differing types of polymeric hydrogel lenses; polymacon, vifilcon, ocufilcon and omnifocon, were capable of delivering an effective dose of timolol maleate which had been passively transferred to the lens.

This invention is principally directed at the passive transfer of an antiglaucomatous medicament into a polymeric hydrogel and this subsequent delivery of this medicament into the ocular fluid of the eye.

The polymeric material of this invention is a polymeric hydrogel which has been described as a hydrophilic polymer capable of forming a hydrogel when contacted with water as disclosed in U.S. Pat. No. 5,256, 751.

It is known to use various polymeric hydrogel lenses with absorbed medicinal agents as medication delivery systems. To be effective for the purposes of this invention, the lens must be a polymeric hydrogel with a water content of about 38–60% by weight and the medicinal agent must be capable of being absorbed in a dilute form into the lens in an amount sufficient to allow a period of sustained delivery of this medication into the ocular fluid. The polymer can be ionic or nonionic. A preferred composition of the polymer is a tetrapolymer of hydroxymethylmethacrylate, ethylene glycol, dimethylmethacrylate, and methacrylic acid. A preferred monomer forming the hydrophilic polymer is the hydroxyester 2-hydroxyethyl methacrylate (HEMA).

Numerous medications are known to be absorbed into a polymeric hydrogel contact lenses and subsequently transferred into the ocular liquid. A preferred additive in this invention is dilute timolol maleate. In this preferred embodiment the dilute timolol maleate is delivered in an aqueous solution to a polymeric hydrogel contact lens in a concentration of 0.68 mg of timolol maleate/mi or a 0.05% concentration of timolol maleate solution at a pH of about 7.0–7.4 for at least three hours, after this contact lens has been washed in saline solution and then dried for at least 15 minutes.

An additional preferred additive in this invention is dilute brimonidine tartrate which is delivered in an aqueous solution to a polymeric hydrogel contact lens in a concentration of 0.2 mg brimonidine tartrate/ml or a 0.02% concentration of brimonindine tartrate solution at a pH of about 7.0–7.4 for at least three hours, after this contact lens has been washed in saline solution and then dried for at least 15 minutes.

In the foregoing the invention has been described in terms of certain preferred embodiments for the purpose of illustration and not limitation. It is to be understood that any changes or modifications obvious to those skilled in the art based on this disclosure are intended to be within the scope of the invention as claimed.

What is claimed is:

1. A drug delivery system comprising a polymeric hydrogel contact lens containing timolol maleate in a concentration of between 0.05% and 0.25% by weight absorbed in said contact lens which is capable of being delivered into the ocular fluid.

2. The polymeric composition of claim 1 wherein said ocular fluid has a pH in the range of between about 7.0–7.4.

3. The polymeric composition of claim 1 wherein said polymeric hydrogel material has a water cotenet in the range of between about 38–60% by weight.

4. The polymeric composition of claim 1 wherein said polymeric hydrogel material includes a tetrapolymer of hydroxymethylmethacrylate, ethylene glycol, dimethylmethacrylate, and methacrylic acid.

5. The polymeric composition of claim 1 wherein the absorbed medicinal agent can be transferred into the ocular fluid at ambient conditions.

6. The polymeric composition of claim 1 wherein the absorbed medicinal agent can be transferred into the ocular fluid at existing conditions.

7. The polymeric composition of claim 1 as a shaped contact lens which retains the ability to correct vision.

8. A drug delivery system comprising a polymeric hydrogel contact lens containing brimonidine tartrate at a concentration of between 0.02% and 0.2% by weight absorbed in said contact lens which is capable of being delivered into the ocular fluid.

9. A The polymeric composition of claim 8 wherein said ocular fluid has a pH in the range of between about 7.0–7.4.

10. The polymeric composition of claim 8 wherein said polymeric hydrogel material has a water content in the range of between about 38–60% by weight.

11. The polymeric composition of claim 8 wherein said polymeric hydrogel includes a tetrapolymer of hydroxymethylmethacrylate, ethylene glycol, dimethylmethacrylate, and methacrylic acid.

12. The polymeric composition of claim 8 wherein the absorbed medicinal agent can be transferred into the ocular fluid at ambient conditions.

13. The polymeric composition of claim 8 wherein the absorbed medicinal agent can be transferred into the ocular fluid at existing conditions.

14. The polymeric composition of claim 8 as a shaped lens wherein the lens retains the ability to correct vision.

15. A process for preparing a polymeric hydrogel contact lens for use which comprises washing the lens in a saline solution; drying the lens for at least about 15 minutes; placing the washed and partially desiccated lens in a dilute aqueous solution of timolol maleate in a concentration of about 0.68 mg of timolol maleate/ml at a pH in the range of between about 7.0–7.4 for approximately three hours; and removing the lens from the solution ready for use in an eye.

16. A process for preparing a polymeric hydrogel contact lens for use which comprises washing the lens in a saline solution; drying the lens for at least about 15 minutes; placing the washed and partially desiccated lens in a dilute aqueous solution of brimonidine tartrate in a concentration of about 0.2 mg of brimonidine tartrate/ml at a pH in the range of between about 7.0–7.4 for approximately three hours; and removing the lens from the solution ready for use in an eye.

17. The drug delivery system of claim 1, wherein said concentration of timolol maleate is 0.25% by weight.

18. The drug delivery system of claim 8, wherein said concentration of brimonidine tartrate is 0.2% by weight.

* * * * *

UNITED STATES PATENT AND TRADEMARK OFFICE
CERTIFICATE OF CORRECTION

PATENT NO. : 6,410,045 B1
DATED : June 25, 2002
INVENTOR(S) : Clyde Lewis Schultz and Janet M. Mint It is certified that error appears in the above-identified patent and that said Letters Patent is hereby corrected as shown below:

Column 1,
Line 15, replace "of of" with -- of --;

Column 3,
Line 66, replace "to as" with -- as --;

Column 6,
Line 22, replace "cotenet" with -- content --.

Signed and Sealed this

Seventeenth Day of June, 2003

JAMES E. ROGAN
*Director of the United States Patent and Trademark Office*